United States Patent
Anderson et al.

Patent Number: 5,527,308
Date of Patent: Jun. 18, 1996

[54] LASER ILLUMINATOR

[75] Inventors: R. Rox Anderson, Lexington, Mass.; Nayantara Bhatta, Skowhegan, Me.; Scott Prahl, Brookline; Peter J. Dwyer, Natick, both of Mass.

[73] Assignee: The General Hospital Corporation, Boston, Mass.

[21] Appl. No.: 384,345

[22] Filed: Feb. 1, 1995

Related U.S. Application Data

[63] Continuation of Ser. No. 35,530, Mar. 22, 1993, abandoned, which is a continuation-in-part of Ser. No. 854,942, Mar. 20, 1992, abandoned.

[51] Int. Cl.$^6$ .................................................... A61B 17/36
[52] U.S. Cl. ............................... 606/14; 606/15; 606/16; 606/17
[58] Field of Search ........................... 606/2, 9, 10, 11, 606/12, 15, 17; 128/665; 607/88, 89, 92, 93

[56] References Cited

U.S. PATENT DOCUMENTS

| | | | |
|---|---|---|---|
| 4,512,762 | 4/1985 | Spears . | |
| 4,556,057 | 12/1985 | Hiruma et al. | 606/14 |
| 4,612,938 | 9/1986 | Dietrich et al. | 128/665 |
| 4,660,925 | 4/1987 | McCaughan, Jr. . | |
| 4,799,479 | 1/1989 | Spears | 606/7 |
| 4,878,492 | 11/1989 | Sinofsky et al. | 606/15 |
| 4,998,930 | 3/1991 | Lundahl | 606/16 |
| 5,041,109 | 8/1991 | Abela | 606/15 |
| 5,042,980 | 8/1991 | Baker et al. . | |
| 5,054,867 | 10/1991 | Wagnieres et al. . | |
| 5,059,191 | 10/1991 | Beyer et al. | 606/2 |
| 5,151,096 | 9/1992 | Khoury . | |
| 5,169,395 | 12/1992 | Narciso . | |
| 5,196,005 | 3/1993 | Doiron et al. . | |

*Primary Examiner*—Stephen C. Pellegrino
*Assistant Examiner*—Sonya Harris-Ogugua
*Attorney, Agent, or Firm*—Fish & Richardson

[57] ABSTRACT

An illuminator including a differential optical radiator and a laser fiber disposed within the differential optical radiator. The differential optical radiator includes a first region that has a first level of reflectivity and a first level of transmissivity and a second region that has a second, higher level of reflectivity and a second, lower level of transmissivity. The first and second regions are positioned such and their reflectivities and transmissivities are chosen such that the radiator produces a substantially uniform pattern of illumination from the first and second regions.

In another embodiment, the illuminator includes an expandable radiator and a laser fiber disposed within the expandable radiator. The reflectivity of the expandable radiator is such that the illumination at the outer surface of the expandable radiator is substantially uniform.

16 Claims, 7 Drawing Sheets

LASER ILLUMINATOR

This invention was made with Government support under Contract N00014-91-C-0084 awarded by the Department of the Navy. The Government has certain rights in the invention.

CROSS-REFERENCE TO RELATED APPLICATION

This is a continuation of application Ser. No. 08/035,530, filed Mar. 22, 1993, now abandoned, which is a continuation-in-part of application Ser. No. 07/854,942, filed Mar. 20, 1992, now abandoned.

BACKGROUND OF THE INVENTION

The invention relates to laser-illuminators used primarily in medical applications.

Lasers can be used to deliver illumination, e.g., diagnostic or therapeutic illumination, to a portion of the body such as a tissue, an organ, or a cavity. An example of therapeutic illumination is photodynamic therapy in which an unactivated agent is administered to a patient and tissue containing the agent is irradiated with light of an appropriate wavelength to activate the agent and kill the illuminated agent-containing tissues.

In photodynamic therapy (PDT), a photosensitizing drug retained in a tissue is excited by an appropriate wavelength light to cause local injury and necrosis of that tissue. Photodynamic action usually requires three components: a photosensitizer, oxygen, and light. Photofrin (PF) is a commonly used photosensitizer. When injected intravaneously, it is taken up and preferentially retained by certain tissues such as neoplastic, inflammatory, traumatized, and embryonic tissues. When excited with light, oxygen inside a cell containing PF converts to singlet oxygen, which results in a toxic effect and cell death. The potential for minimal normal tissue toxicity (because of selective sequestration of PF within tumors) has prompted PDT treatment of skin, bladder, head and neck, brain, and esophageal tumors. Much of the selectivity of PDT is based on vascular uptake, and cell death is due to vascular injury and thrombosis.

The use of PDT for gynecological cancers, although not extensive, has been encouraging. Preferential Photofrin uptake and retention as demonstrated by fluorescence has been reported in both dysplasia and cervical carcinomas. Primary and recurrent vaginal cancers, cervical, and ovarian tumors have been treated by PDT.

The endometrium is a highly vascular tissue that undergoes cycles of neovascularization and thus shares some properties with common solid tumors. Recent discoveries indicate that the endometrium also takes up and retains Photofrin in preference to surrounding tissue including the myometrium.

SUMMARY OF THE INVENTION

In one aspect, generally, the invention features a laser-illuminator including a differential optical radiator and a laser fiber disposed within the differential optical radiator. The differential optical radiator includes a first region having a first level of reflectivity and a first level of transmissivity and a second region having a second, higher level of reflectivity and a second, lower level of transmissivity, with the first and second regions being positioned and their reflectivities and transmissivities chosen such that the differential optical radiator produces a substantially uniform pattern of illumination from the first and second regions.

In preferred embodiments, the radiator is a rigid body; the radiator is expandable, flexible, or expandable and flexible; a third region is included with the reflectivity and transmissivity of the third region chosen such that the radiator produces a pattern of illumination including a lower level of illumination from the third region; the illumination produced by the third region is substantially uniform; the radiator is adapted for insertion into a body cavity; the dimensions of the radiator are approximately equal to the dimensions of the body cavity; the radiator is sized for insertion into the uterus; the radiator is transparent to light of a predetermined wavelength and includes a coating that diffusively reflects light of the wavelength applied to the radiator; the coating includes a heat resistant paint; the illuminator further includes a travel-limiting member at the proximal end of the radiator; the fiber includes a diffusively reflective coating, preferably the coating has a region of relatively high reflectivity and a region of relatively low reflectivity; the coating includes a heat resistant paint; and the illuminator is incorporated into a uterine dilator.

The illumintor of the invention can be used in a method of irradiating a body cavity including the steps of placing the distal end of the illuminator in the body cavity and transmitting light through the fiber of the illuminator.

In preferred embodiments, the method further includes the step of measuring the body cavity and dimensioning the radiator of the illuminator to fit within the body cavity, and the step of delivering a photosensitive dye to the body cavity prior to transmitting light through the fiber of the illuminator.

In another aspect, the invention includes a method of performing endometrial ablation comprising the steps of providing the illuminator described above, inserting the distal end of the illuminator into the uterus, and transmitting light through the fiber of the illuminator to irradiate the inner surface of the uterus.

In another aspect, generally, the invention features a laser-illuminator including an expandable radiator and a laser fiber disposed within the expandable radiator, where the reflectivity of the expandable radiator is chosen such that the illumination at the surface of the expandable radiator is substantially uniform.

In preferred embodiments, optimal uniformity of illumination is obtained by optimal positioning of the fiber within the expandable radiator; uniformity of illumination is further enhanced by optimally positioning multiple fibers within the expandable radiator; the expandable radiator is expanded with a transparent fluid; the expandable radiator is flexible; the expandable radiator is shaped to apply illumination to a surface such as the skin; the expandable radiator is shaped to apply illumination to the interior of a blood vessel; the expandable radiator is shaped to apply illumination to an irregularly shaped cavity; the expandable radiator is sized and shaped to apply illumination to a body cavity; the expandable radiator is sized and shaped to apply illumination to a body cavity of a particular patient; the expandable radiator is sized and shaped to apply illumination to a uterus; the expandable radiator is sized and shaped to apply illumination to a mouth; the expandable radiator is sized and shaped to apply illumination to an esophagus; the expandable radiator is sized and shaped to apply illumination to nasal passages; the fiber produces and the expandable radiator reflects visible light; the fiber produces and the expandable radiator reflects infrared; the fiber produces and the expandable radiator reflects ultraviolet; and the expandable radiator reflects energy produced by the source.

The illuminator of the invention can be used in a method of irradiating a body cavity including the steps of placing the distal end of the illuminator in the body cavity, expanding the expandable radiator, and transmitting light through the fiber of the illuminator.

In preferred embodiments, the method further includes the step of measuring the body cavity and dimensioning the expandable radiator of the illuminator to fit within the body cavity, and the step of delivering a photosensitive dye to the body cavity prior to transmitting light through the fiber.

In another aspect, the invention includes a method of performing endometrial ablation comprising the steps of providing a laser-illuminator including an expandable radiator, inserting the distal end of the illuminator into the uterus, expanding the expandable radiator, and transmitting light through the fiber of the illuminator to irradiate the inner surface of the uterus.

Photosensitive agent, dye, or toxin, as used herein, refers to a substance which is substantially non-toxic to a target tissue prior to irradiation, but which becomes toxic to the tissue upon irradiation of the target tissue.

Transmitted light refers to light, which having impinged on the inner surface of a radiator reaches the outer surface of the radiator. Transmissivity refers to the ability of a surface or structure to transmit incident/diffuse light.

Reflectivity refers to the ability of a surface or structure to reflect a portion of incident/diffuse light. As used herein, a reflective surface or structure refers to a diffusively reflective surface or structure, i.e., one which randomizes or scatters the reflected light. Reflectivity and transmissivity are inversely correlated.

In preferred embodiments, the reflectivity of the wall of the expandable radiator is 60% or more, in more preferred embodiments the reflectivity is 75% or more, in even more preferred embodiments the reflectivity is 85% or more, 90% or more, or 95% or more, and in the most preferred embodiments the reflectivity is 99% or more.

Similarly, the absorption of the expandable radiator in preferred embodiments is 5% or less, in more preferred embodiments the absorption is 3% or less, in even more preferred embodiments the absorption is 1% or less, or 0.5% or less, and in the most preferred embodiments the absorption is 0.1% or less.

A differential optical radiator is an optical radiator having a nonuniform pattern of reflectively, i.e., the reflectivity of the optical radiator varies with location on the radiator, providing regions of relatively high reflectivity and regions of relatively low reflectivity. Since transmissivity is essentially inversely correlated with reflectivity, a pattern of reflectivity gives rise to a pattern of transmission and thus illumination. Since reflectivity also increases the number of internal reflections (and thus randomizes the light incident on the inner surface of the optical radiator) the uniformity within a region of a given reflectivity is maximized. The reflectivity at the point of (or region of) greatest reflectivity on a differential optical radiator is at least 5% greater than the reflectivity at the point on (or region of) the differential optical radiator with the lowest reflectivity (where the percent difference is determined as one hundred times the reflectivity at the point (or region) of highest reflectivity divided by the reflectivity at the point (or region) of lowest reflectivity). In preferred embodiments, the difference is greater than 10%, in more preferred embodiments the difference is greater than 20%, and in the most preferred embodiments the difference is greater than 40%.

A substantially uniform field of illumination is one in which the intensity of light (measured in $Wcm^{-2}$ at the exterior surface of the radiator) does not vary by more than 50% between the two most disparate points of the radiator surface, or the two most disparate points of a region (see below). In preferred embodiments the variation is less than 20%, in more preferred embodiments the variation is less than 10%, in even more preferred embodiments the variation is less than 5%, and in the most preferred embodiments the variation is less than 1%. Illumination can be uniform over the entire surface of the radiator or it can be uniform within a region. For example, a radiator can have three regions, one with a low level of reflectivity that produces a high level of illumination, one with an intermediate level of reflectivity that produces an intermediate level of illumination, and one with a high level of reflectivity that produces a low level of illumination. The level of illumination within one or more of the regions should be substantially uniform.

The degree of uniformity required generally depends on the use to which the illuminator is being put. For example, when the illuminator is being used in photodynamic treatment of the uterus, variations of as much as 50% are acceptable. Meanwhile, when used in treatment of the mouth (which is typically more sensitive), variations of more than 20% are probably unacceptable.

The invention features illuminators which deliver a desired pattern of laser light. The pattern can have either a substantially uniform distribution of illumination or a controlled, non-uniform distribution of illumination. The illuminator can include a differential optical radiator that is characterized by a pattern of regions of different reflectivities that give rise to a desired pattern of illumination. Alternatively, the illuminator can include a highly reflective uniform optical radiator that gives rise to a uniform pattern of illumination.

The invention allows for control of the pattern of light emitted by the radiator, even when the radiator is of a contorted or highly irregular shape or when the light source is not centrally placed within the radiator. The invention allows for specific patterns of illumination to be created.

The illuminators can be used in any procedure or process in which irradiation is desired. In particular, they can be used in medical procedures. For example, they can be used to irradiate a hollow body cavity or organ, (e.g., the uterus, mouth, esophagus, bladder, or bronchus); a surface such as the skin; or the interior of a blood vessel. The illuminators are particularly advantageous for endometrial ablation in the treatment of dysfunctional uterine bleeding and other symptoms of endometrial disorders. The illuminators can be easily inserted through the vagina and cervix, providing a non-invasive procedure which can often treat endometrial conditions which otherwise would require a hysterectomy.

Other features and advantages of the invention will be apparent from the detailed description and from the claims.

DETAILED DESCRIPTION

The drawings are first described.

Drawings FIG. 1 is a plan view of a laser-illuminator according to an embodiment of the invention.

FIG. 4a is a side view of the balloon of the inducer tube/balloon assembly of FIG. 4.

CONTROLLED PATTERNS OF DIFFUSE ILLUMINATION

Figure 1:
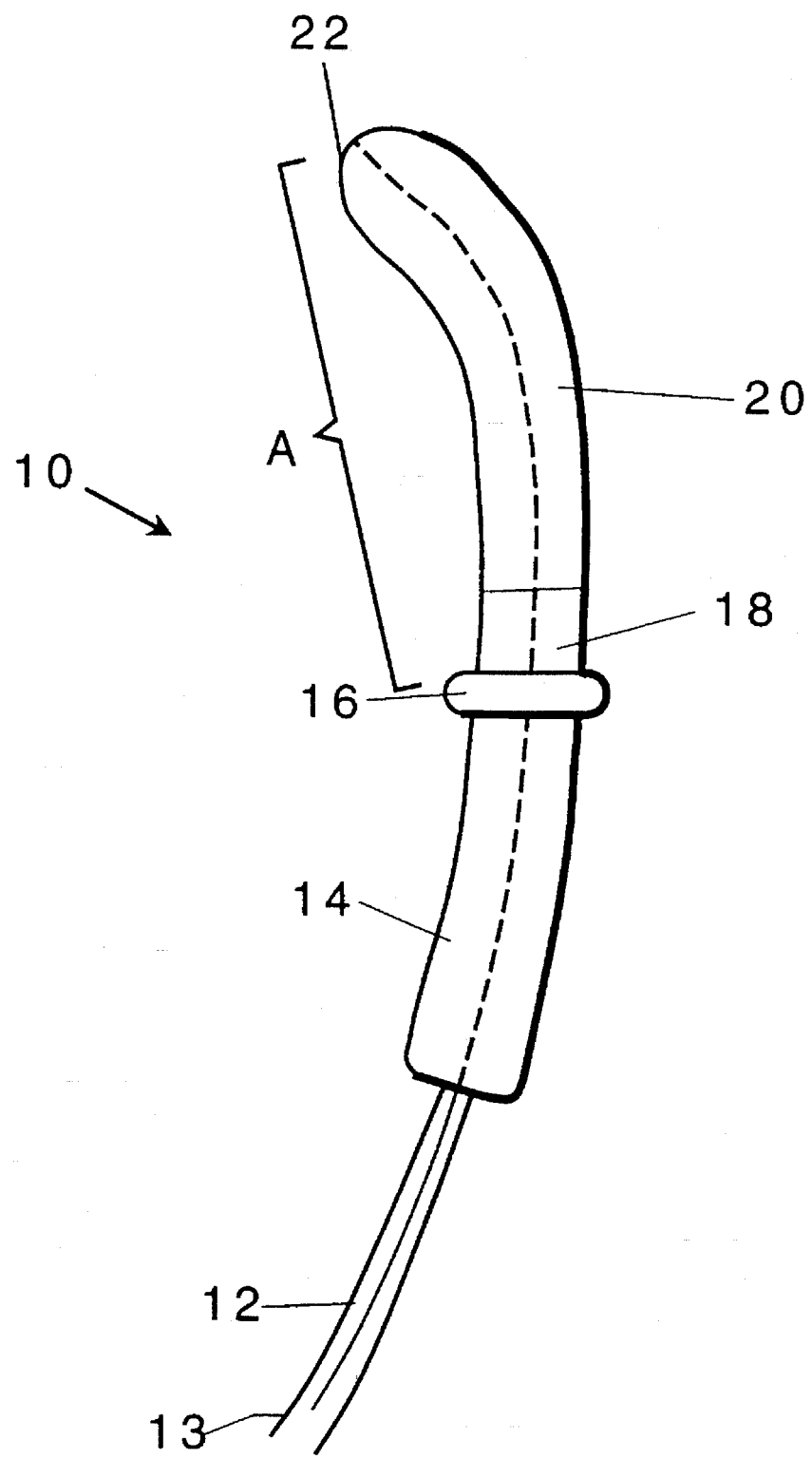

Control of the pattern of light produced by an illuminator is critical in many applications. For example, when the illuminator is used in photodynamic treatment of photosensitized tissue, the intensity of illumination is correlated with the extent of photodynamic killing of target cells or tissue. Higher levels of illumination result in more killing while lower levels result in less of killing. An illuminator that produces an unwanted or unintentionally uneven pattern of illumination, such as a pattern that includes a hot spot (a region of relatively high illumination), can result in excessive destruction at the tissue site adjacent to the hot spot. Cold spots arise in areas characterized by relatively low illumination. A cold spot can result in insufficient tissue killing in tissue adjacent to the cold spot.

Unwanted variations in the pattern of illumination arise from a number of sources, including variations in the distance between the light source (usually a laser fiber) and the target tissues or the inner surface of the radiator, directionally non-random emission of light from the laser fiber, and the shape of the radiator.

Manipulation of the ratio of reflectivity to transmissivity of the radiator can be used to achieve a uniform pattern of illumination. For example, if the light source within a radiator is closer to a portion of the radiator, more photons will strike that portion. With a radiator of high transmissivity and low reflectivity, a relatively large proportion of the photons striking the radiator would be transmitted out of the radiator. In that case, the increased number of photons striking the portion of the radiator closest to the light source could result in a hot spot. By increasing the reflectivity (and concomitantly decreasing the transmissivity) of the radiator, a photon will be subject to an increased number of internal reflections before passing out of the radiator. After a number of internal reflections, the photons would be transmitted over a larger area of the radiator. This, in turn, would avoid production of a hot spot and would lead to a more uniform pattern of illumination.

Generally, the optical characteristics of the radiator should be as follows. Diffusive reflectivity should be high in comparison to transmissivity, so that internal reflection and the concomitant uniformity of the transmitted light is maximized. Absorption should be minimized to prevent heat build up and to maximize efficiency.

The desired optical properties can be imparted to the radiator by depositing, for example, paint or other pigment, quartz or alumina powder, or other metal powder, in or on the wall of the radiator. Generally, reflectivity in an area is increased by increasing the amount of deposited material.

Differential Optical Radiator

In one embodiment, the invention includes a differential optical radiator. The pattern of light produced by the differential optical radiator can be controlled by controlling the absorption, reflectivity, and transmissivity of portions of the radiator.

Local manipulation of the reflectivity of the differential optical radiator can be used to achieve a uniform pattern of illumination in the face of substantial differences in the quantities of photons striking different portions of the radiator. For example, if a fiber used as a light source produced a controlled beam of photons from its end, a hot spot could be produced at the area being struck by the projected beam. By increasing the reflectivity of the area being struck by the beam, the beam can be reflected to other portions of the radiator and the hot spot can thereby be avoided.

In some applications, a pattern of various intensities is desirable. Local manipulation of the reflectivity of the differential optical radiator can also be used to achieve a desired non-uniform pattern of illumination. For example, if greater or lesser illumination is desired at a given point, the reflectivity can be adjusted to give the desired level of illumination at that point. The reflectivity of a region and of the rest of the differential optical radiator contribute to uniformity of the region. In other words, reflectivity at any point effects the uniformity of the entire radiator.

Structure

Referring to FIG. 1, illuminator 10 includes laser fiber 12, differential optical radiator 18 surrounding the distal end of laser fiber 12, insulating sleeve 14, disposed proximally of the proximal end of differential optical radiator 18, buffer material 13 surrounding the length of laser fiber 12 proximally of insulating sleeve 14, and limiting member 16 interposed at the junction of differential optical radiator 18 and insulating sleeve 14.

Laser fiber 12 is preferably an unclad fiber, i.e. a fiber which lacks any cladding on its outer circumferential surface such that the fiber can emit laser light over its length. Alternatively, a conventional clad fiber may be obtained, and the cladding stripped from an area of a desired length (the area which is to emit light) extending proximally from the distal end of the fiber. Where, as shown, the entire length of laser fiber 12 is unclad, insulating sleeve 14 and buffer 13 surround the portion of the fiber which will not be inside the body cavity to prevent emission of light and to allow safe handling of illuminator 10. Insulating sleeve 14 provides a gripping surface for the user, and is preferably a resilient material, e.g., rubber. Buffer 13 may be any material which prevents emission of light, and is preferably a flexible material for ease of manipulation.

The portion of laser fiber 12 which will be inside the body cavity to be irradiated (marked "A" in FIG. 1) is preferably coated with a coating that diffuses light emitted by laser fiber 12. This coating is preferably a heat resistant paint, but may be any coating which causes light diffusion. The thickness of the coating is determined experimentally for each application, by applying thin layers of the coating until a build-up is achieved which produces the desired amount of diffusion.

Differential optical radiator 18 further diffuses light emitted by laser fiber 12. Radiator 18, which is preferably a material which is transparent to light of the wavelength which is to be used, is coated on its inner or outer surface with a coating 21 that diffusively reflects light emitted by laser fiber 12. This coating may be the same as or different from the coating on laser fiber 12, as desired. The thickness of the coating is determined using the same method as described above for coating laser fiber 12. Different thicknesses may be provided in different areas of the housing to vary the reflectivity (and thus transmissivity) of a chosen region of differential optical radiator 18. For example, in illuminator 10, used for irradiating the pear-shaped internal cavity of the uterus, a less reflective thinner coating (or fewer layers of coating) is applied to area 20 than to area 22. This limits the effect of light emitted from the distal end of laser fiber 12 which, if coatings of similar reflectivity were applied to areas 20 and 22, could result in a hot spot at area 22. An even thicker coating (i.e., more reflective and less transmissive) is applied to area 18 which is inside the cervical area during use and which therefore should emit minimal light.

The length of differential optical radiator 18, and, similarly, the length of the unclad, coated portion of laser fiber 12, is approximately equal to the length of the cavity to be irradiated. The width or circumference of differential optical radiator 18 is preferably approximately equal to that of the cavity, so that differential optical radiator 18 fits snugly into the cavity. These dimensions may be determined by direct measurement or by other means.

Limiting member 16 is interposed between differential optical radiator 18 and insulating sleeve 14. Member 16 acts as a stop, preventing over-insertion of illuminator 10 into the body cavity, as over-insertion could result in tissue damage.

A preferred use for the device illustrated in FIG. 1 is endometrial ablation using photodynamic therapy. A preferred photosensitizer is a hematoporphyrin e.g., Photofrin II.

Expandable Optical Radiator

In another embodiment, the invention includes a highly reflective expandable optical radiator that produces a substantially uniform pattern of light. Typically, the expandable optical radiator is expanded with transparent fluid such as air or saline solution. In most cases, the expandable optical radiator is also flexible, which allows it to conform to irregularly shaped body cavities such as the uterus, nasal passages, and mouth. To further ease conformity with irregularly shaped cavities, the expandable optical radiator is usually pre-shaped to a shape similar to the relevant cavity. Thus, the expandable optical radiator is not typically a regular sphere or cylinder.

Even when the expandable optical radiator is irregularly shaped, it generates a substantially uniform pattern of light by relying on the large number of internal reflections resulting from use of highly reflective materials. As the shape of the expandable optical radiator becomes less regular (i.e., becomes less like a sphere or cylinder), the reflectivity is increased to maintain the same level of uniformity. Due to the high reflectivity, expandable optical radiator also requires low absorption (as the number of internal reflections increases, the degree of absorption must be decreased to avoid excessive heating of the expandable optical radiator). In some embodiments, the absorption may need to be less than one percent.

As described below, a preferred expandable optical radiator is made from a white material that reflects visible light. However, as desired, infrared or ultraviolet reflecting materials or materials that reflect different wavelengths of the electromagnetic spectrum could be used.

Structure

Figure 2:
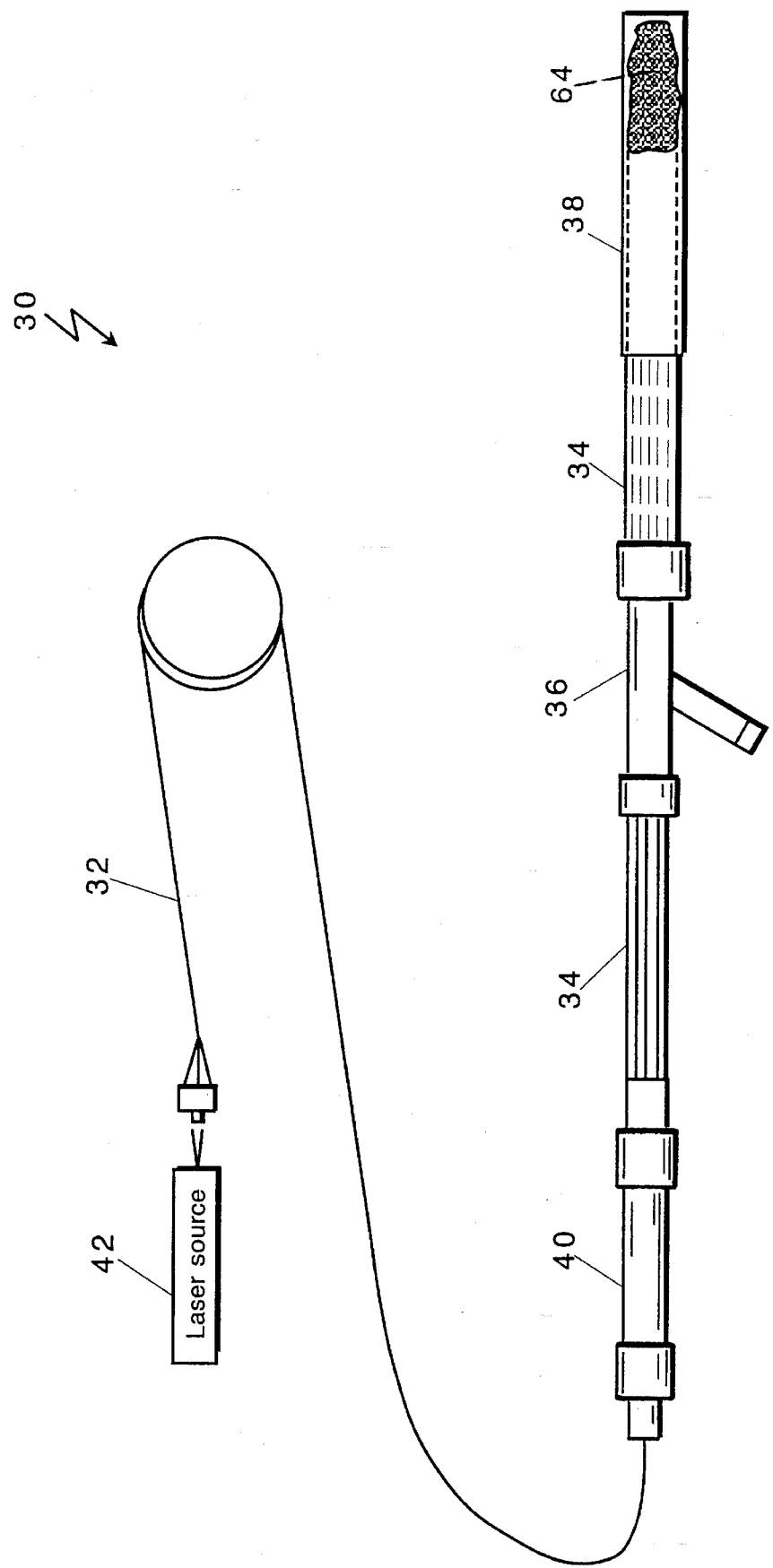
FIG. 2 is a plan view of a laser-illuminator according to another embodiment of the invention.

Referring to FIG. 2, a uterine light diffuser system 30 includes a silica optical fiber assembly 32, a plastic optical fiber assembly 34, a coupling and fluid access assembly 36, a balloon/inducer tube assembly 38 including a balloon 64 (shown deflated), and a connector assembly 40. The individual assemblies and their relationship to one another are discussed below. Briefly, silica optical fiber assembly 32 transmits laser radiation from a laser source 42 at the proximal end of uterine light diffuser system 30 to the plastic optical fiber assembly 34 via connector assembly 40. Plastic optical fiber assembly 34 extends from a connector assembly 40, through coupling and fluid access assembly 36, and into balloon/inducer tube assembly 38 at the distal end of light diffuser system 30.

Figure 3:
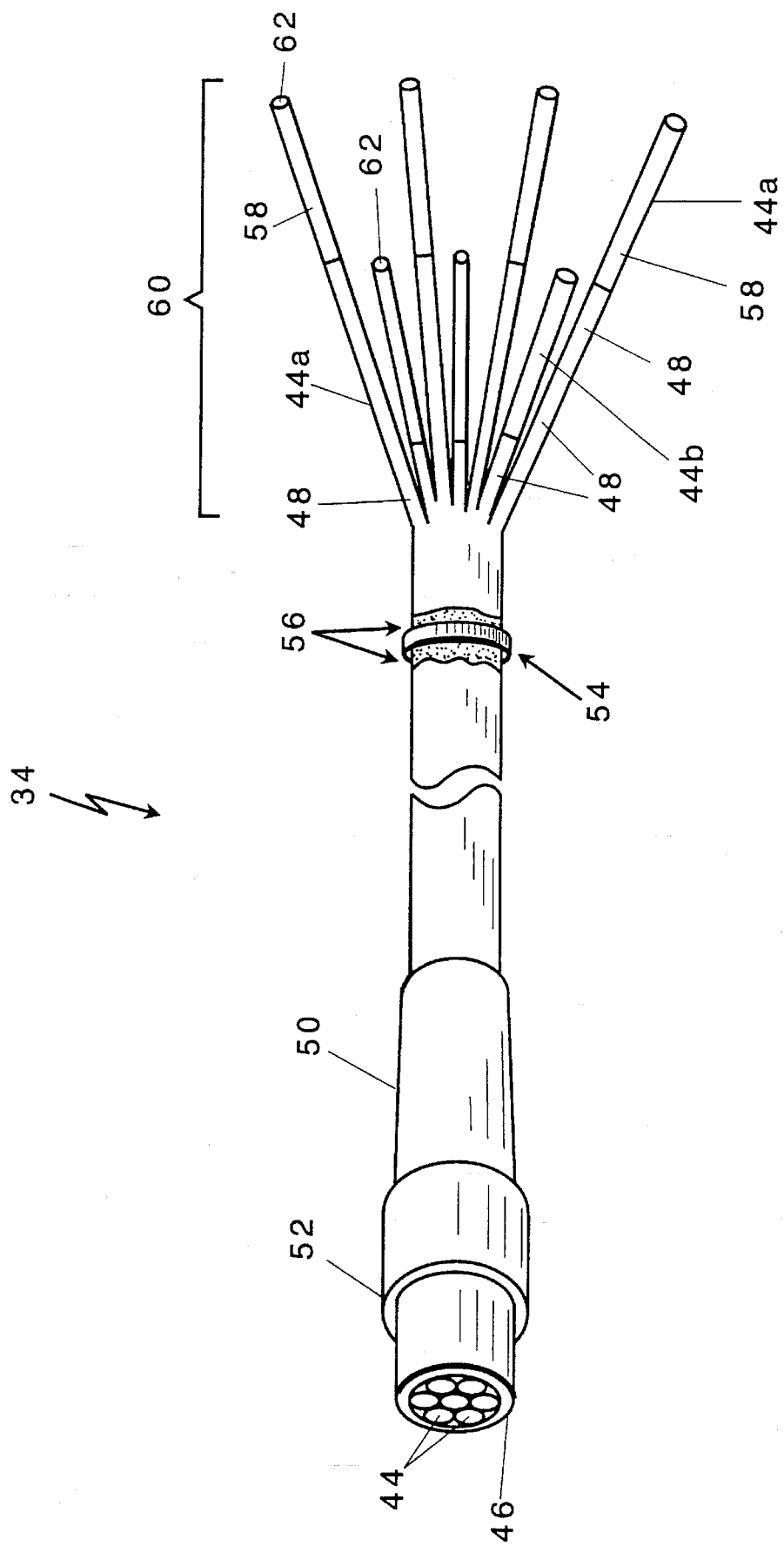
FIG. 3 is a plan view of a plastic optical fiber assembly of the illuminator of FIG. 2.

Referring to FIG. 3, plastic optical fiber assembly 34 includes seven plastic optical fibers 44 arranged in a "six around one" configuration at the proximal end 46 of assembly 34. The circular shape resulting from the six around one configuration increases the efficiency with which light energy is transferred from the silica fiber of silica fiber assembly 32 to fibers 44. At the proximal end, fibers 44 are bundled using a sleeve 50. A connector 52 holds and positions fibers 44 at the proximal end for coupling of irradiated power from silica optical fiber assembly 32.

Near the distal end, a retaining member 54, e.g., a Teflon heat shrink band, maintains fibers 44 in a desired orientation that is based, in part, on the patient's uterine dimensions. Retaining member 54 is preshrunk to avoid heat damage to fibers 44. Medical grade UV cure epoxy 56 secures retaining member 54 to fibers 44.

At the distal end, fibers 44 are oriented to optimize uniformity of illumination at the exterior of balloon 64. Thus, for example, if a single fiber 44 were employed, the single fiber 44 would be oriented in the central axis of balloon 64. When, as shown in FIG. 3, multiple fibers 44 are employed, fibers 44 are arranged so as to occupy a plane that approximately divides balloon 64 into a top half and a bottom half. Within this plane, fibers 44 are spread out to approximate the shape of balloon 64.

Typically, plastic optical fibers 44 are coated with a plastic cladding 48. Plastic cladding 48 is removed, e.g., by acetane or mechanical abrasion, from about 2.0 cm of the distal portion 60 of each plastic optical fiber 44. To allow light emission through the sides of the distal portions 60, the unclad portions of fibers 44 are scratched using, for example, fine sandpaper. Similar amounts of cladding 48 are removed from each fiber 44 to ensure that each fiber 44 produces a similar level of illumination. If desired, cladding 48 could also be removed from the proximal portions of fibers 44.

After removal of cladding 48 and attachment of retaining member 54, fibers 44 are arranged in a desired pattern. As shown in FIG. 3, the distal portions 60 of the seven fiber configuration are arranged in a planar 4:3 orientation with four longer fibers 44a and three shorter fibers 44b that each emit light 2.0 cm down their length. Fibers 44 are spread out in a predetermined pattern which is dependent on the patient's uterine dimensions. Fibers 44 are spaced in relationship to one another and to balloon 64 (not shown) of balloon/inducer tube assembly 38 to ensure substantially uniform radiation at the surface of balloon 64.

The desired orientation of fibers 44 can be obtained in the following manner. First, the bundle of fibers 44 is attached, using pins or other means, to a flat surface. Next, fibers 44 are arranged as desired and secured using additional pins or other means. Thereafter, fibers 44 are "set" in this orientation by pouring water heated to between 70°–80° C. over fibers 44. (This same procedure can be repeated to modify the orientation of fibers 44 if, as discussed below, testing determines that the fibers produce an unsuitable pattern of illumination.)

Preferably, all fiber tips 62 are conically shaped to avoid emission of a controlled beam of photons. However, fiber tips 62 are not sharp.

Seven fibers 44 are used because they allow for a six around one configuration that, as noted above, increases the efficiency with which light energy is transferred to fibers 44. As is also discussed above, used of seven fibers 44 allows fibers 44 to be oriented in a manner that is particularly useful for uniformly illuminating an irregularly shaped body cavity such as the uterus. (If efficient transfer of light energy were the only concern, a single fiber 44 would provide the optimal configuration.)

An example of a suitable plastic optical fiber 44 is one having a polymethyl methacrylate core 58, a fluorinated polymer cladding 48, an overall length of about 40 cm, and an outer diameter of 750 microns. Such a fiber is available from the Nichimen Corp. Connector 52 can be made from stainless steel, with an outer diameter of 7.8 millimeters and a length of 3.05 centimeters. A suitable connector is the SMA 905 Connector available from Amp, Inc. Retaining member 54 can be fabricated from medical grade tetrafluoroethylene with a length of 5 millimeters and a recovered dimension of 2.250 millimeters. Suitable material is available from Zeus, Inc. Acrylate and urethane methacrylate, e.g., Loctite Adhesive 18007, Loctite Corp., are suitable for epoxy 56.

Figure 4:
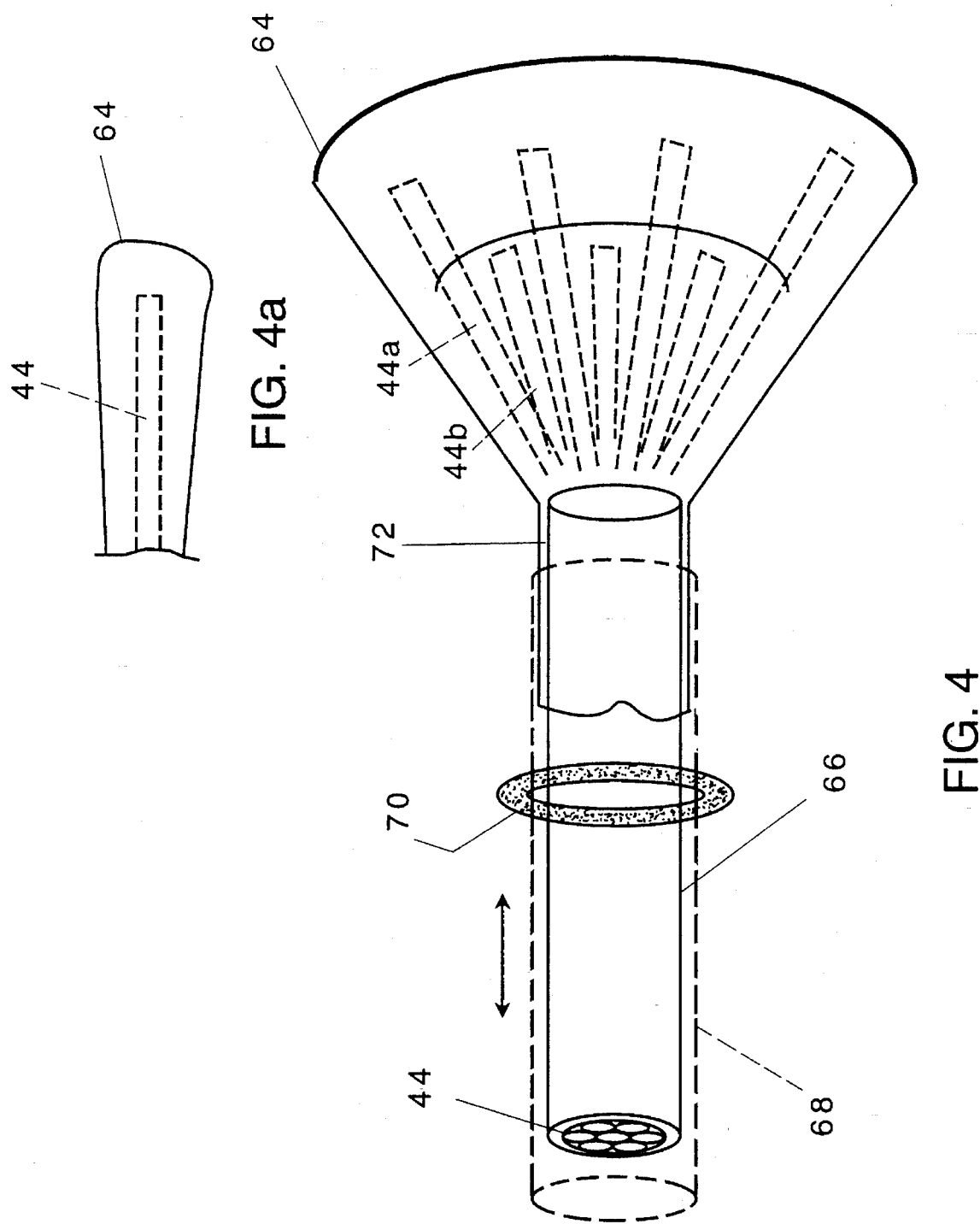
FIG. 4 is a plan view of an inducer tube/balloon assembly of the illuminator of FIG. 2.

Referring to FIG. 4, silicon balloon/inducer tube assembly 38 includes balloon 64 (shown expanded), inner tube 66, outer inducing sheath 68, and length gauging ring 70. Balloon 64 is attached to the distal end 72 of inner tube 66. Inner tube 66 extends from within coupling and fluid access assembly 36 (see FIG. 2) distally toward the distal end of uterine light diffuser system 30. Inner tube 66 provides a passage for plastic optical fibers 44 and saline solution used to expand balloon 64. Plastic optical fibers 44 are oriented to conform with the shape of balloon 64. As shown in FIG. 4a, fibers 44 are located in a plane near the central axis of balloon 64. Inner tube 66, with plastic optical fibers 44 inside, slides inside outer inducing sheath 68, which contains fibers 44 and balloon 64 (which is rolled up for insertion) during insertion of the device into the patient's uterus. In most case, the device is inserted using ultrasonic guidance.

After insertion into the uterus, outer inducing sheath 58 is withdrawn from its initial position by a predetermined amount to expose balloon 64 in the uterus. The predetermined amount depends on the length of the patient's uterus and is determined, for example, using ultrasonic imaging. Next, balloon 64 is carefully expanded to the proper volume and pressure.

Length gauging ring 70 is positioned on outer inducing sheath 68 according to the patient's uterine dimensions so as to allow proper initial placement of balloon 64 in the patient's uterus so as to prevent perforation. The initial placement is designed to prevent any light from illuminating the patient's cervix. Once inducing sheath 68 is withdrawn and balloon 64 is expanded, balloon 64 prevents further penetration of the device into the uterus.

Balloon 64 is manufactured using a lost wax technique. In the first step, the patient's uterine dimensions are determined through, for example, use of an ultrasound procedure. Next, a wax model based on these dimensions is created. The model can be either custom sized or selected from a set of predetermined standard sized models. The wax model is then smoothed. Smoothing can be by flame polishing or by hand, in which case the model is smoothed until the wax begins to feel slippery. A technique that has been particularly successful is for the modeler to heat his hands using a hot-plate or other means prior to smoothing. Next, distal end 72 of inner tube 66 is slightly flared by inserting a soldering iron into distal end 72 or other means and the wax model is attached thereto. Flaring of distal end 72 allows for more secure attachment of the wax model. If desired, a fiber for monitoring the reflectivity of balloon 64 can be attached to the wax model such that the fiber will become embedded in balloon 64 during manufacture.

Balloon 64 is made from a medical grade silicone material. A white scattering powder such as alumina ($Al_2O_3$) that allows uniform light distribution into the uterus is added to the silicone material. During manufacture, the silicone and alumina are mixed, in a hooded environment, with an appropriate amount of the ether. The ratio of ether to silicone is selected to minimize the effects of air bubbles produced by the evaporation of ether while maintaining the viscosity of the mixture at a desired level. Particular amounts that have proved successful are 6.0 ccs of silicone and 20.5 ccs of ether to which are added 1.25 grams of alumina. These amounts of materials have proved adequate for building a single layer on three balloons.

The mixture of ingredients is produced in the following manner. After the ingredients are combined, they are premixed using a spatula or other device. Next, the mixture is placed in a device such as a vortex and mixed thereby. After removal from the vortex, the mixture is further combined using a Fisher Sonic Dismembrator Model 300 (a high frequency, high power sonicator) set at 35% for about one minute. This final step reduces clumping of alumina particles. The mixture is then poured into a beaker and allowed to set for about one minute so as to allow the large quantity of air bubbles resulting from initial evaporation to escape.

The wax model is then dipped into the mixture. The mixture, and eventually balloon 64, chemically attaches to inner tube 66 by silicone to polyurethane bonding. After removal from the mixture, inner tube 66 is held at about a forty five degree angle with the wax model facing down over the beaker. Inner tube 66 is then slowly rotated for about one minute to eliminate drip marks. The wax model is held over the beaker so that ether fumes from the mixture in the beaker can react with the mixture attached to the model. This reaction makes the mixture on the model flow and further eliminated drip marks. Elimination of drip marks is important because a balloon 64 having consistent thickness is desired.

Thereafter, the coated wax model is placed in a cooler containing ice and allowed to cure overnight. Reduced temperature slows down the curing process and reduces the occurrence of air bubbles in balloon 64. Ice is placed in the cooler both for its cooling effect and because it adds water vapor that also improves the curing process.

After curing, the dipping process is repeated to create a balloon 64 consisting of multiple layers. The number of layers used is the number necessary to produce the desired reflectivity without making balloon 64 inflexible. Currently, balloons having from three to twelve layers have been employed. As each layer is added, balloon 64 becomes less flexible. When all desired layers have been added and cured, the wax is removed from balloon 64 by soaking balloon 64 in boiling water and repeatedly flushing balloon 64.

A suitable material for inner tube 66 is medical grade polyurethane. A suitable tube has an outer diameter of 3.05 mm, an inner diameter of 2.50 mm, and an overall length of approximately 21 cm. Such a tube is available from Putnam Plastics.

A suitable material for balloon 64 is medical grade silicone RTV available from Dow/Corning. Typical dimensions are as follows: length, approximately 4 cm; height, largest section, approximately 2.5 cm; smallest section, approximately 3.5 mm; thickness, approximately 4.0 mm; and balloon material thickness, approximately 0.089 mm. Suitable white scattering material is an inert $Al_2O_3$ 0.3 micron ceramic dust, such as is manufactured by Union Carbide and distributed by Beuhler as Micropolish A 0.3 micron Alpha Alumina.

A suitable material for outer inducing sheath 68 is medical grade Teflon (tetrafluoroethylene) such as is available from Zeus Inc. Suitable dimensions are as follows: outer diameter, 3.78 mm; inner diameter, 3.38 mm; and overall length, approximately 25 cm.

Length gauging ring 60 can be fabricated from plastic. Suitable dimensions are as follows: width, 7.6 mm; height, 12.7 mm; length, 6.35 mm.

Figure 5:
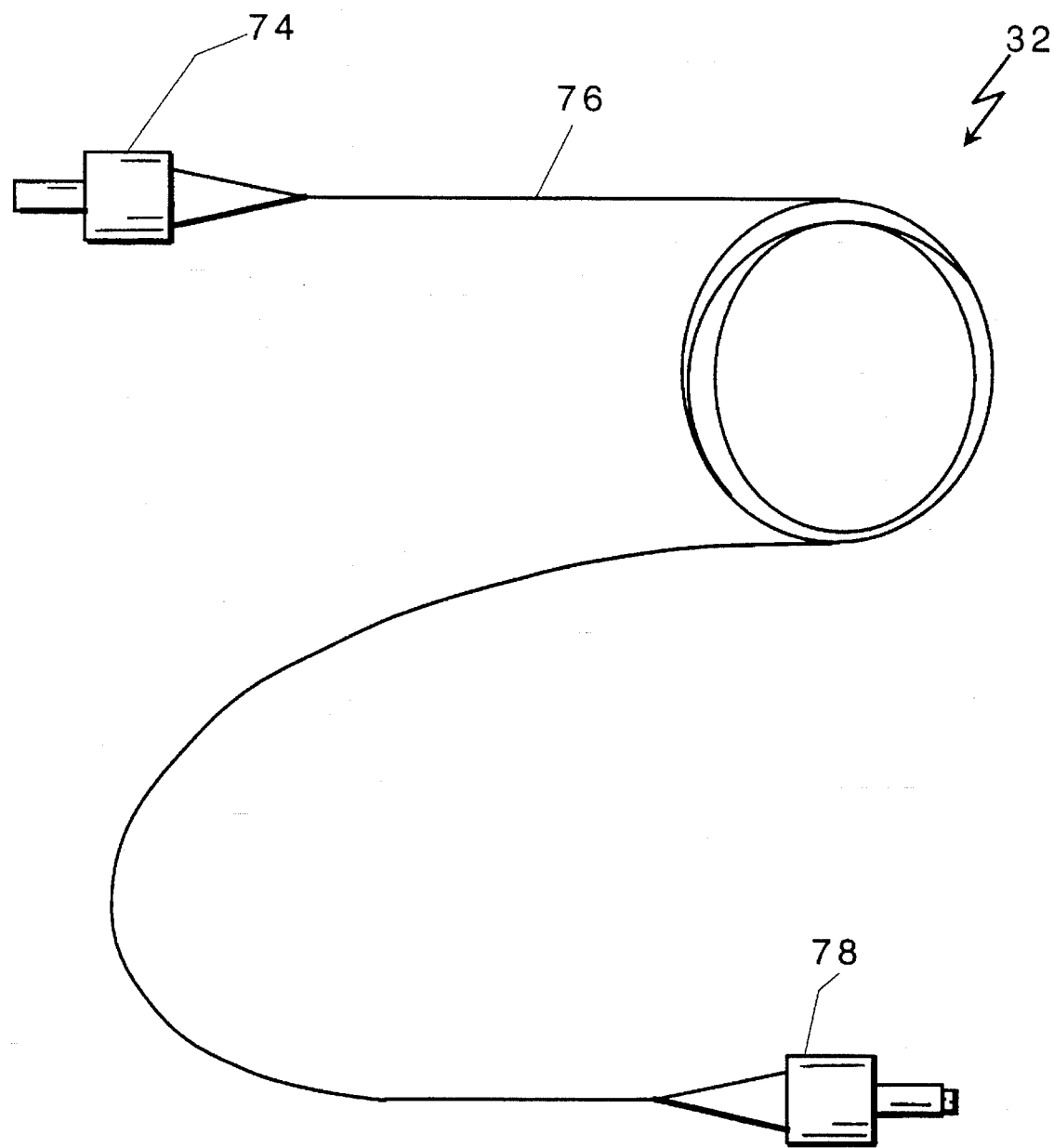
FIG. 5 is a plan view of a silica optical fiber assembly of the illuminator of FIG. 2.

Referring to FIG. 5, silica optical fiber assembly 32 includes proximal connector 74, optical fiber 76, and distal connector and lens assembly 78. Typically, optical fiber 76 is a 600 micron core diameter, 630 micron clad diameter, fused silica fiber with a 1040 micron Tefzel (Dupont) buffer. Optical fiber 76 is approximately five meters in length. Proximal connector 74, a stainless steel SMA 905 optical fiber connector, couples optical fiber 76 to laser source 42 (see FIG. 2). An optical lens is disposed within distal connector and lens assembly 78, and housed in a stainless steel sheath that is threaded onto the Tefzel buffer of optical fiber 76. The lens assembly is then positioned into a SMA 905 connector to form distal connector and lens assembly 78. Distal connector and lens assembly 78 is coupled to the proximal end of plastic optical fiber assembly 34 via connecting assembly 40.

Suitable fused silica fibers are available from Ensign Bickford Fiber Optics (P/N HCN-M0600T-14). Suitable optical fiber connectors typically have a stainless steel body with a PVC boot, e.g., those made by made by Amp, Inc., (P/N SMA 905 style 699-SPC-0162-01) (outer diameter, 7.8 mm; overall length, 3.05 cm). Suitable lenses are known to those skilled in the art, e.g., as available from Ensign Bickford Fiber Optics, (lens, glass; outer housing, stainless steel; outer diameter, 9.52 mm; overall length, 9.52 mm).

Referring again to FIG. 1, connecting assembly 40 includes a SMA 905 mated pair coupling. The separation distance between the two mating connectors is specified to allow the laser beam from optical fiber 76 (via the lens in distal connector and lens assembly 78) to diverge to the size of the bundled plastic optical fibers 44 (shown in FIG. 3). The connectors from silica optical fiber assembly 32 and plastic optical fiber assembly 34 are simply threaded onto connecting assembly 34 until they are finger tight. A suitable connector coupling is made by Storm Products Inc./Amp Inc. (stainless steel body; outer diameter, 6.35 mm; overall length, approx. 3.3 cm).

Figure 6:
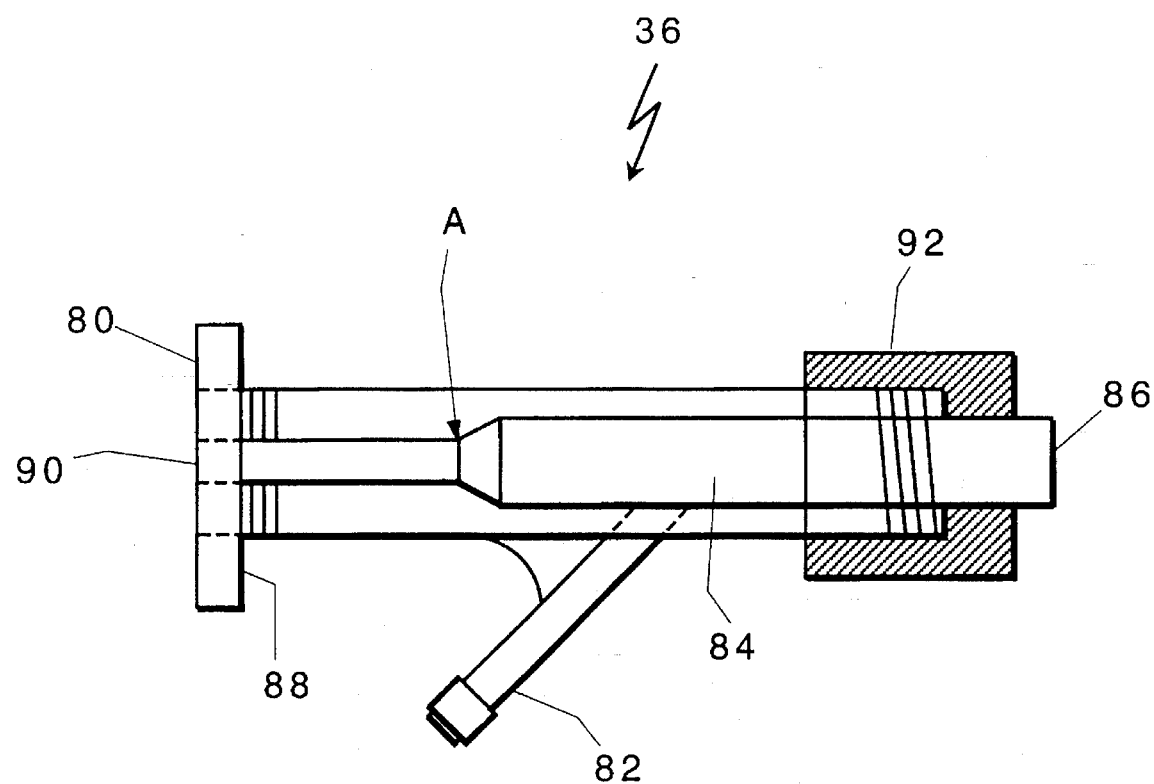
FIG. 6 is a plan view of a coupling and fluid access assembly of the illuminator of FIG. 2.

Referring to FIG. 6, coupling and fluid access assembly 36 includes proximal end 80, fluid access port 82, lumen 84, distal end 86, compression ring 88, and fiber exit port 90. At point A, lumen 84 is dimensioned to allow passage of seven bundled plastic fibers 44 (see FIG. 3). Fibers 44 then pass through fiber exit port 90. Compression ring 88 prevents movement of plastic optical fiber assembly 34, which passes through coupling and fluid access assembly 36 and into silicon balloon/inducer tube assembly 38 (see FIG. 2).

Inner tube 66 of silicon balloon/inducer tube assembly 38 is connected to distal end 86 of coupling and fluid access assembly 36 through a Luer-Loc fitting such that fluid access port 82 is continuous with balloon 64 of silicon balloon/inducer tube assembly 38 (see FIG. 2). As a result, fluid access port 82 allows saline solution to be supplied for expanding balloon 64. Saline solution can be supplied to fluid access port 82 via a 12 cc syringe. If desired, the pressure and volume in balloon 64 can be monitored (apparatus not shown).

Coupling and fluid access assembly 36 can be fabricated from clear plastic at an overall length of about 7.5 cm. For example, a plastic Touhy Borst Adapter with a side port fitting, as made by TTI Inc./Medical Disposables International Inc., is suitable.

Testing of the Balloon

Prior to manufacture and use of balloon 64, the reflectance, transmittance, and absorbance of the silicone material being employed should be tested. One procedure for doing this includes the following steps. First, a control balloon is manufactured using the technique described above. The control balloon is then dissected in half so that a single layer of silicone material can be spectrally tested using a spectrophotometer such as a Beckman UV 5270 over a range of wavelengths including the wavelength of interest. For example, where 630 nm is the wavelength of interest, the range of spectral analysis could be from 600 nm to 650 nm. In tests performed on a sample made from the materials described above, the reflectivity at 630 nm was 73.2% and the transmissivity was 21.8%. Because absorbance equals one minus the sum of transmissivity and reflectivity:

$$A=1-(T+R)$$

the absorbance for the material was 5.0%.

After manufacture and prior to use, each balloon 64 must be tested. Characteristics tested include integrity, absorption, and uniformity of light intensity. Integrity can be tested, for example, by expanding balloon 64 to a pressure that substantially exceeds that encountered during normal use. Thereafter, balloon 64 can be monitored for leaks or deformities.

Absorption can be tested by monitoring the temperature of balloon 64 while supplying different input powers from laser source 42. The temperature of balloon 64 can be monitored using a calibrated thermal camera. The temperature of an acceptable balloon 64 should not vary as the supplied input power is modified over a range of anticipated input powers, e.g., from 500 mWatts to 1.3 Watts. Also, the temperature of balloon 64 should not be affected even when the maximum input power, e.g., 1.3 Watts, is supplied for a minimum of 25 minutes.

When used in performing endometrial ablation and other procedures, the light intensity at the outer surface of balloon 64 must be substantially uniform. An apparatus for measuring the uniformity of the light intensity is depicted in FIGS. 7 and 8.

Figure 7:
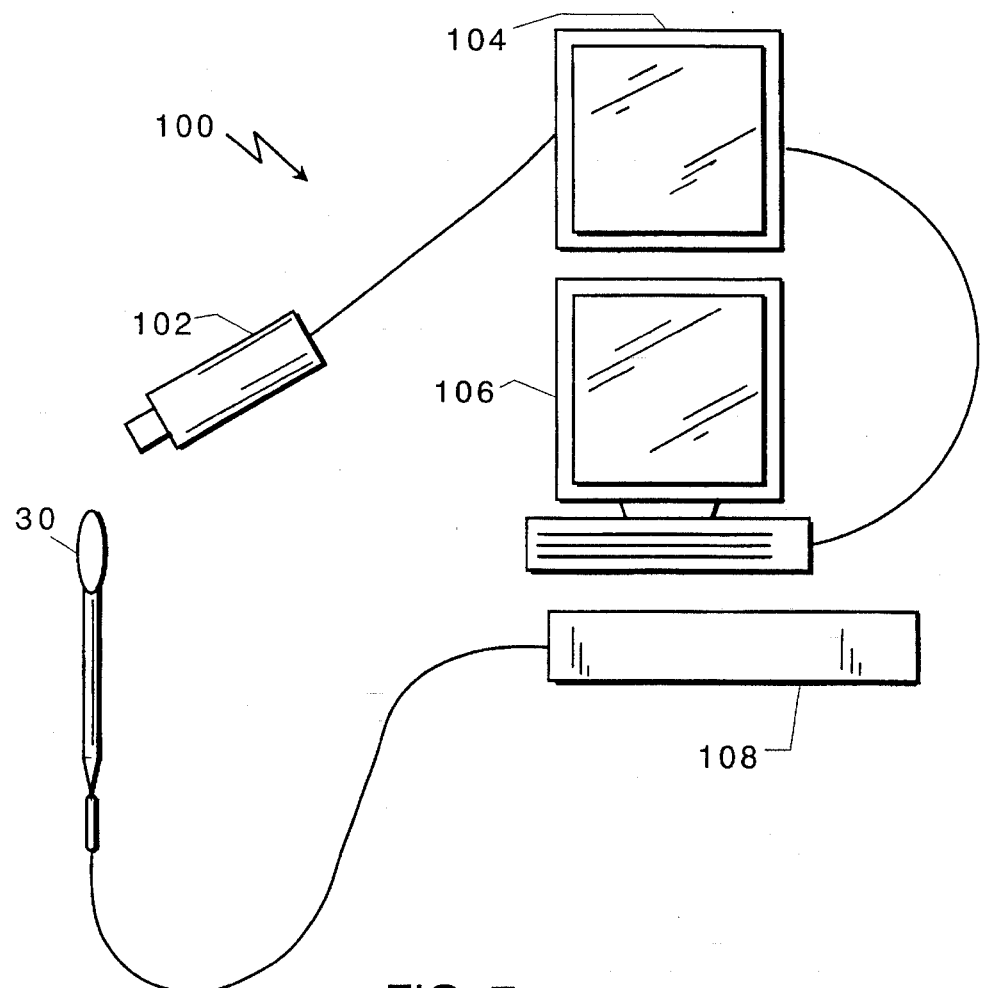
FIG. 7 is a plan view of an apparatus for testing the illuminator of FIG. 2.
Figure 8:
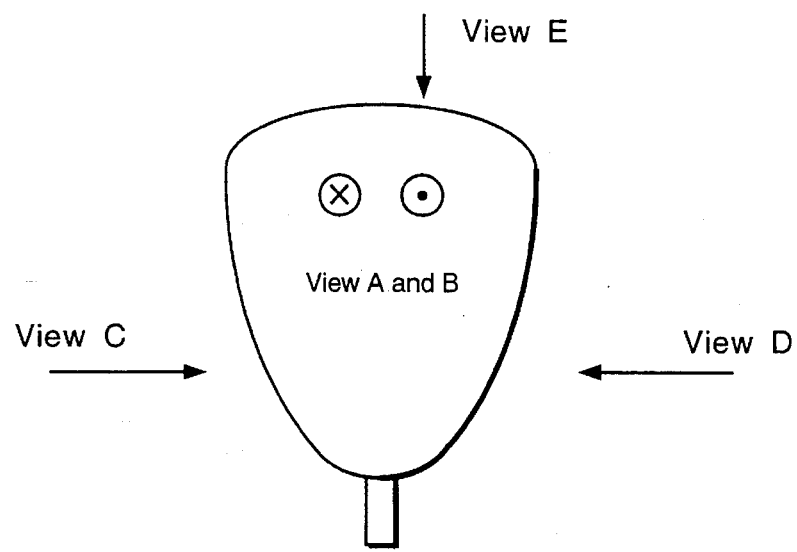
FIG. 8 illustrates test points used by the apparatus of FIG. 7.

Referring to FIG. 7, a uniformity test apparatus 100 was used to measure intensity profiles of a uterine light diffuser 30. A linear based black and white CCD camera 102 coupled to a monitor 104 and a computer 106 captures a video image of uterine light diffuser 30 while diffuser 30 was illuminated from an Argon pumped dye laser (APDL) 108 at a wavelength of 690 nm. CCD camera 102 had a 0.3 optical density neutral density filter to avoid saturation in camera 102 and in image processing software (Image-Pro Plus) in computer 106. The range of the image processing software dictated the 0.3 optical density neutral density filter.

The imaging processing software measured the gray scale of an input image with 8 bit accuracy. Thus, a pixel value of 0 intensity corresponded to absolute black and a pixel value of 255 intensity corresponded to absolute white. The video board of computer 106 and CCD camera 102 were tested for linearity prior to conducting the uniformity test.

The plastic optical fibers in the balloon were oriented to conform with the size and shape of the balloon using the procedure discussed above. For test purposes, the fibers were further oriented to optimize uniformity. When an orientation optimized uniformity for one surface of the balloon, it also optimized uniformity for all other surfaces.

The balloon tested was imaged from five different views, as shown in FIG. 8. Each view has raw data analysis and median filtering data analysis. The raw data analysis results were from untampered data pixel points, and included error pixels in the image data. Because there are a certain number of unwanted pixels due to camera and software errors, the median filtering data analysis corrected for single, stray error pixels that were surrounded by constant, uniform pixels (when a single pixel is surrounded by largely different intensity pixels, this indicates that the pixel is an error).

Variables for statistical uniformity or non-uniformity of corresponding views are as follows: $I_{max}$=maximum intensity; $I_{min}$=minimum intensity; $I_o$=initial intensity; $X=(I_{max}-I_{min})/(I_{avg}-I_o)$, where $I_{avg}$ is the mean and $I_o=0$ in this case); and Y=Standard Deviation/Mean. This test produced the following results:

View A:
  Raw Data
    Minimum Gray Scale Intensity: 69
    Maximum Gray Scale Intensity 134
    Mean of all data points: 99.03
    Standard Deviation: 18.32
    X=0.656
    Y=0.185
  Median Filtering
    Minimum gray Scale Intensity: 72
    Maximum Gray Scale Intensity: 127
    Mean of all data points: 100.4
    Standard Deviation: 17.67
    X=0.656
    Y=0.185
View B:
  Raw Data
    Minimum Gray Scale Intensity: 95
    Maximum Gray Scale Intensity: 213
    Mean of all data points: 142.1
    Standard Deviation: 28.32
    X=0.830
    Y=0.199
  Median Filtering
    Minimum Gray Scale Intensity: 88
    Maximum Gray Scale Intensity: 208
    Mean of all data points: 139.7
    Standard Deviation: 27.98
    X=0.859
    Y=0.200
View C:
  Raw Data
    Minimum Gray Scale Intensity: 108
    Maximum gray Scale Intensity: 215
    Mean of all data points: 154.1
    Standard Deviation: 27.38
    X=0.694
    Y=0.178
  Median Filtering
    Minimum Gray Scale Intensity: 107
    Maximum gray Scale Intensity: 194
    Mean of all data points: 148.1
    Standard Deviation: 21.21
    X=0.587
    Y=0.143
View D:
  Raw Data
    Minimum Gray Scale Intensity: 63
    Maximum gray Scale Intensity: 129
    Mean of all data points: 92.39
    Standard Deviation: 16.39
    X=0.714
    Y=0.177
  Median Filtering
    Minimum Gray Scale Intensity: 70
    Maximum gray Scale Intensity: 116
    Mean of all data points: 89.39
    Standard Deviation: 14.95
    X=0.515
    Y=0.167
View E:
  Raw Data
    Minimum Gray Scale Intensity: 73
    Maximum gray Scale Intensity: 220
    Mean of all data points: 148.4
    Standard Deviation: 35.35
    X=0.990
    Y=0.238
  Median Filtering
    Minimum Gray Scale Intensity: 79
    Maximum gray Scale Intensity: 215
    Mean of all data points: 145.3
    Standard Deviation: 32.27
    X=0.936
    Y=0.222

In this test, the best observed value of X was approximately 50% uniformity and the best observed value of Y was approximately 86% uniformity. The two values differ primarily because X takes the maximum difference between the two extreme points in each view while Y uses the standard deviation as a set value. X and, to a lesser extent, Y can be improved by altering the positioning of fibers 44 within balloon 64 or by increasing the reflectivity of balloon 64.

After testing, uterine light diffuser system 30 is gas sterilized and packaged with a hermetic seal. No uterine light diffuser 30 is ever reused.

Use

Uterine light diffuser system 30 is used in performing photodynamic endometrial ablation as an alternative to a hysterectomy, particularly in the case of dysfunctional uterine bleeding. There are over 600,000 hysterectomies performed per year in the United States. The main indications are leiomyomas and dysfunctional uterine bleeding. Abnormal bleeding accounts for 18–40% of the hysterectomies. The complications of hysterectomy apart from accompanying physical, social, and psychological effects are 0.1% mortality and up to 30% morbidity.

Safety Precautions

Photodynamic agents, e.g., Photofrin and its predecessor, Hpd, are known to cause skin photosensitivity which may be present for 4–6 weeks or longer after injection. Since there have been rare instances of severe sunburn in patients treated with Photofrin polyporphyrin, precautions must be taken to prevent exposure to direct sunlight for 30 days after injection. Patients must also be draped during transport.

Patients should be advised to stay indoors, cover exposed parts of their bodies and protect eyes from direct sun rays, strong fluorescent or incandescent lighting (i.e. a dentist's lamp or examining light) or strong residential direct indoor lighting (i.e., direct spotlight, floodlight, etc.) for this period. After 30 days they may expose a small area of skin to the sun for 15 minutes (or more) to test for residual sun sensitivity. There is no proof that sunscreens are of value. Patients should be warned to avoid cone or helmet-type hairdryers for 30 days after Photofrin injection, as extreme heat may activate the Photofrin retained in the scalp and produce a photosensitivity-type reaction with erythema and induration. Patients should be given instruction regarding precautions required following Photofrin injection.

Precautions should be taken with high power lasers as defined by the guidelines in the American National Standard Institute Publication for the Safe Use of Lasers in Health Care Facilities. Patients and investigators should wear laser safety goggles which are designed to filter out 630 nm light, as should all other personnel in the room as recommended by the FDA. Unnecessary personnel should not be allowed in the room where the laser is used.

To avoid injury due to heat, all optical coupling points should be located outside of the patient.

Dose

The minimum effective dose of Photofrin and the maximum light dose should be used in order to excite all photosensitizer present in the endometrium. The majority of studies in humans with PDT have shown positive response with 2–2.5 mg/kg of Photofrin and a photodynamic endometrial ablation experiment in an animal model has shown better response with 2 mg/kg dose of Photofrin. Thus, a preferred dosage is about 2 mg/kg dose of Photofrin. Based on endometrial ablation experiments with a rabbit model, 100 J/cm$^2$ of laser light irradiation should be sufficient to excite all the photosensitizer present in the endometrium. By increasing the light dose, one might be able to excite more Photofrin in the endometrium and achieve improved clinical response with a given dose of Photofrin. Dosage can be precisely determined using an initial dosage and light intensity and increasing each if there is not a complete response according to set criteria.

The following table shows an initial drug and light dose along with higher levels to be used if a given level fails to give the desired degree of ablation.

| Drug Dose | Light Dose | Escalation Criteria |
| --- | --- | --- |
| 1.5 mg/kg | 150 J/cm$^2$ | If no response or partial response go to next level |
| 1.5 mg/kg | 200 J/cm$^2$ | If no response or partial response go to next level |
| 2 mg/kg | 150 J/cm$^2$ | If on response or partial response go to next level |
| 2 mg/kg | 200 J/cm$^2$ | |

Photofrin for injection can be supplied in 75 mg vials as sterile polyporphyrin freeze-dried powder by QLT, Inc. Vancouver, BC, Canada V52 4H5. To constitute, 30 mls of 5% dextrose for injection, USP, should be added for a final concentration of 2.5 mg/ml. For each kilogram of body weight, 0.8 cc should be given (1.5–2 mg/kg) as an i.v. infusion over no less than 3 minutes. Photofrin should not be reconstituted with saline solutions and should be protected from sunlight, e.g., by storing in the dark under refrigeration at 2°–8° C. (36°–46° F.). Photofrin can also be injected intravenously at 2.0 mg/kg (slow i.v. push, injection should take 3.5 minutes and may be given through a "Y" tube of an IV saline drip). Patients should receive medications that are clinically indicated, except for chemotherapeutic agents.

Quantification of light dose

Therapeutic light doses and administration can be quantified as follows. Fiber optic transmission can be tested by measuring the power output with an integrating-sphere power meter. The laser output power from the device should be 1.8–3.0 watts, and the output obtained will be at least 80% of the input power. The laser light should be delivered in a diffuse manner from a length of 4–5 cm. The irradiance should be kept below 0.2 W/cm$^2$ to avoid thermal injury (this is only slightly greater irradiance than common sunlight). The light dose can be determined as follows:

$$\text{Fluence (light dose)} = \text{Irradiance} \times \text{exposure time}$$
$$(\text{Joules/cm}^2) \quad (\text{Watts/cm}^2) \quad (\text{seconds})$$

The time required to get the desired fluence of 100 J/cm$^2$ in the uterine cavity is given by $$\text{Time (in seconds)} = \frac{100 \text{J/cm}^2}{\text{irradiance (W/cm}^2)}$$

Power output should be checked again immediately after the treatment.

A 20 Watt Coherent Inova 900 argon-ion pumped dye laser is a suitable source of 630+/–3 nm light. A coherent laser power meter and a monochromator can be used for all measurements of laser power, and to verify that the wavelength is 630+/–3 nm. The power meter and monochromator should be calibrated to ensure accurate measurements.

Other embodiments are within the claims. For example, in an alternate embodiment, the differential optical radiator may be a material which has optical properties that will diffuse light, e.g. a filled plastic.

What is claimed is:

1. An illuminator comprising
    a highly reflective, expandable radiator having inner and outer surfaces, said outer surface being flexibly configured so that when said expandable radiator is expanded, said outer surface substantially conforms to a shape of a body cavity to be illuminated, and a substantial portion of said inner surface provides a high, diffuse reflectivity for a light field while transmitting a portion of the field, and
    a laser fiber, disposed within said expandable radiator, for delivering the light field to said inner surface of said expandable radiator,
    the reflectivity of said inner surface being sufficiently high such that illumination of the body cavity with the transmitted portion of the light field by said conformed outer surface is substantially uniform.

2. The illuminator of claim 1, wherein said laser fiber is positioned substantially in the center of said expandable radiator.

3. The illuminator of claim 1, wherein said illuminator includes a plurality of laser fibers.

4. The illuminator of claim 1, said illuminator including a means for expanding said expandable radiator with a transparent fluid.

5. The illuminator of claim 1, wherein said expandable radiator, once expanded, comprises a substantially flat portion shaped to provide illumination to a skin surface.

6. The illuminator of claim 1, wherein said expandable radiator, once expanded, comprises a substantially cylindrical portion shaped to provide illumination to an interior of a blood vessel.

7. The illuminator of claim 1, wherein said expandable radiator is irregularly shaped to provide illumination to an irregularly shaped cavity.

8. The illuminator of claim 1, wherein said body cavity is a uterus.

9. The illuminator of claim 1, wherein said laser fiber produces and said expandable radiator reflects visible light.

10. A method of irradiating a body cavity comprising the steps of providing said illuminator of claim 1, placing a distal end of said illuminator in the body cavity, expanding said expandable radiator of said illuminator, and transmitting a light field through said laser fiber of said illuminator so that the light field is delivered to said inner surface of said expandable radiator and then transmitted by said outer surface of said expandable radiator to irradiate the body cavity.

11. The method of claim 10, wherein the method further comprises the step of measuring said body cavity and dimensioning said expandable radiator of said illuminator to fit within said body cavity.

12. The method of claim 11, further comprising the step of delivering a photosensitive dye to said body cavity prior to transmitting light through said laser fiber.

13. A method of performing endometrial ablation comprising the steps of providing said illuminator of claim 1, inserting a distal end of said illuminator into a uterus of a patient, expanding said expandable radiator of said illuminator, and transmitting a light field through said laser fiber of said illuminator so that the light field is delivered to said inner surface of said expandable radiator and then transmitted by said outer surface of said expandable radiator to irradiate an inner surface of the uterus.

14. The illuminator of claim 1, wherein said reflectivity of said portion of said inner surface is greater than 60%.

15. The illuminator of claim 14, wherein said reflectivity of said portion of said inner surface is greater than 95%.

16. The illuminator of claim 1, wherein the entire inner surface provides a high, diffuse reflectivity for the light field while transmitting a portion of the field.

* * * * *